April 20, 1971 J. SPEK Plant Pat. 3,051
ROSE PLANT
Filed May 8, 1969
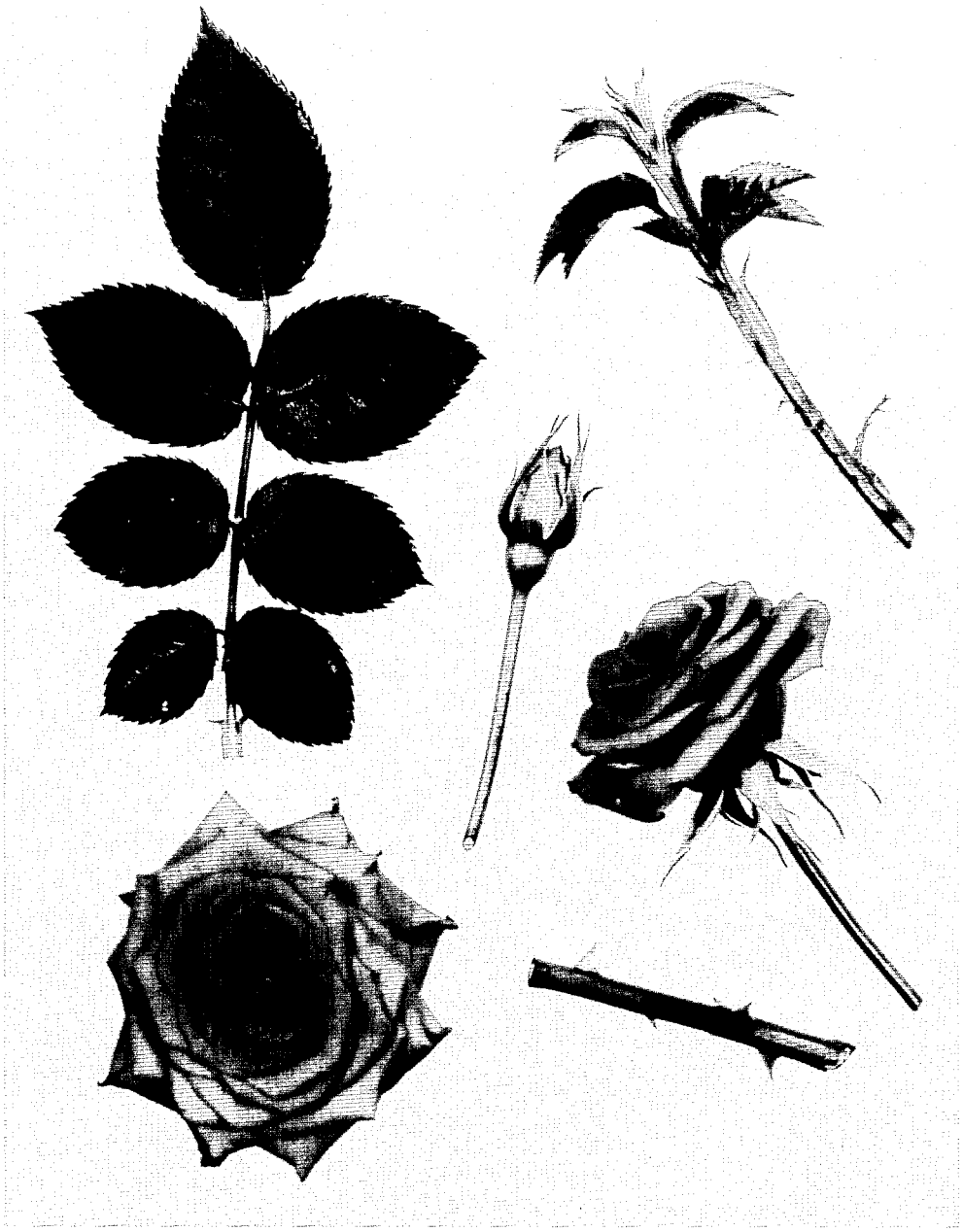
Inventor.
Jan Spek
By: Robb & Robb
Attorneys.

United States Patent Office

Plant Pat. 3,051
Patented Apr. 20, 1971

3,051
ROSE PLANT

Jan Spek, Boskoop, Netherlands, assignor to Jackson & Perkins Company, Newark, N.Y.

Filed May 8, 1969, Ser. No. 823,194
Int. Cl. A01h *5/00*
U.S. Cl. Plt.—29 1 Claim

The present invention relates to a new and distinct variety of rose plant of the floribunda class, which was discovered by me as a sport of the rose variety known as "Nordia" (U.S. Plant Patent No. 2850).

At the time of my discovery, I was growing the variety "Nordia" in my nursery at Boskoop, Holland, and while tending the same, my attention was attracted to one particular plant which bore some flowers of a color significantly different than the color of the flowers on the rest of the plant and the other plants of "Nordia." Upon close inspection of that particular plant, I found that it had sported, and I thereupon took steps to carefully preserve the sport and to keep it under close observation. In due course, I asexually reproduced the sport by budding, as performed in my nursery at Boskoop. Continued observations and tests of the new sport and the progeny derived therefrom have convinced me that it is a new and distinct variety which is definitely distinguished from its parent, as well as from all other rose varieties of which I am aware, as evidenced by the following unique combination of characteristics which are outstanding in the new sport:

(1) A similarity substantially identical in all respects to the parent variety "Norida," except for the color of the buds and open flowers;
(2) A capability of being forced without going "blind";
(3) A continuous blooming habit under forcing conditions; and
(4) A distinctive, attractive, truer and deeper red color of the buds and open flowers, corresponding to near Cardinal Red, as compared to the lighter and more Scarlet Red flower color of "Nordia."

Additional asexual reproduction of the new variety by budding, as performed on my behalf at Newark, N.Y., U.S.A., shows that the foregoing characteristics and distinctions come true to form and are established and transmitted through succeeding propagations.

The accompanying drawing shows typical specimens of the foliage, stems and flowers of my new variety in different stages of development, and as depicted in color as nearly true as it is reasonably possible to make the same in a color illustration of this character.

The following is a detailed description of my new variety, with color terminology in accordance with Wilson's Horticultural Colour Chart, except where general color terms of ordinary dictionary significance are obvious:

Parentage: Sport of "Nordia."
Classification:
*Botanical.*—Rosa hybrid.
*Commercial.*—Floribunda.
Propagation: Holds its distinguishing characteristics through succeeding propagations by budding.

*Flower*

(Observations made from specimens grown in a greenhouse at Newark, N.Y., U.S.A., late in the month of April, during the afternoon.)
Blooming habit: Recurrent—continuous.
Bud:
*Size.*—Medium.
*Form.*—Short; pointed.
*Color.*—When sepals first divide—Purple Madder, Plate 1028. When half-blown—inside of petals—Near Cardinal Red, Plate 822; reverse of petals—Chrysanthemum Crimson, Plate 824/3.
*Sepals.*—Lightly appendaged; hairy edge.
Color—Inside—Green, with whitish hair; outside—Green.
Receptacle.—Color—Green. Shape—Funnel. Size—Large relative to size of flower. Surface—Smooth.
Peduncle. — Length — long. Surface—smooth. Strength—erect; stiff. Color—Light green.
*Opening.*—Opens slowly; outer petals roll back on edges.

Bloom:
*Size.*—Medium; about 2½ inches in diameter.
*Borne.*—Both singly and several together.
*Stems.*—Medium length.
*Form.*—High-centered.
*Petalage.*—From 45 to 50 petals under normal conditions.
*Color.*—Center of flower—upper side of petals—Color is uniform from center to outer petals and from half-open to full-open stages, with color being near Cardinal Red, Plate 822, but being a deeper and truer red. Reverse of petals—Chrysanthemum Crimson, Plate 824/3. Base or petals—small white area at base, with some white streaks extending therefrom on outer petals. General tonality from a distance—Cardinal Red, Plate 822.
*Discoloration (third day).*—Between Cardinal Red Plate 822 and Chrysanthemum Crimson, Plate 824/3.
Petals:
*Texture.*—Thick; leathery.
*Surface.*—inside—velvety; reverse—smooth; color is more dull.
*Shape.*—Round.
*Form.*—Edges slightly quilled.
*Arrangement.*—Imbricated.
*Petaloids in center.*—Few.
*Persistence.*—Drop off cleanly.
*Lasting quality.*—On the plant—very long.
*Fragrance.*—Slight.

*Reproductive organs*

Anthers: Medium size; mixed with petaloids. Color—Yellow.
Filaments (threads): Short. Color—Yellow.
Pollen: Color—Lemon yellow.
Styles: Bunched; uneven length; short.
Stigmas: Color—White.
Ovaries: All enclosed in calyx.
Fruit: None observed.

*Plant*

Form: Bush.
Growth: Vigorous; upright.
Foliage: Compound of 5–7 leaflets.
*Size.*—Large.
*Quantity.*—Normal.
*Color.*—New foliage—Scheele's Green, Plate 860/3 when very young, becoming overlaid with reddish pigment as leaflets unfold. Old foliage—Darker than Spinach Green, Plate 0960.
*Leaflets.* — Shape — oval pointed. Texture — upper side—glossy; under side—smooth; ribs and veins—slightly impressed; edge—serrated; serration—single; petiole — Rachis — color — Green; under side—smooth; stipules—short.

*Disease resistance.*—Resistant to mildew, as determined by comparison with other rose varieties grown under the same conditions at Newark, N.Y., U.S.A.

Wood:

*New wood.*—Color—Light green; bark—smooth.

*Old wood.*—Color—Green; bark—smooth.

Thorns:

*Thorns*—Quantity—On main stalks from base—ordinary; on laterals from stalk—ordinary; form—broad base; color (when young)—transparent; position—irregular.

*Prickles.*—None.

*Short needles.*—Few on main stalks.

I claim:

1. A new and distinct variety of rose plant of the floribunda class, substantially as herein shown and described, characterized particularly as to novelty by the unique combination of a similarity substantially identical in all respects to the parent variety "Nordia," except for the color of the buds and open flowers, a capability of being forced without going "blind," a continuous blooming habit under forcing conditions, and a distinctive, attractive, truer and deeper red color of the buds and open flowers, corresponding to near Cardinal Red, as compared to the lighter and more Scarlet Red flower color of "Nordia."

No references cited.

ROBERT E. BAGWILL, Primary Examiner